(12) United States Patent
Schoenmeyer et al.

(10) Patent No.: US 9,990,713 B2
(45) Date of Patent: Jun. 5, 2018

(54) DETECTING AND VISUALIZING CORRELATIONS BETWEEN MEASURED CORRELATION VALUES AND CORRELATION REFERENCE VALUES OF A PATHWAY

(71) Applicant: Definiens AG, Munich (DE)

(72) Inventors: Ralf Schoenmeyer, Gilching (DE); Sonja Althammer, Burghausen (DE); Guenter Schmidt, Munich (DE)

(73) Assignee: Definiens AG, Munich (DE)

( * ) Notice: Subject to any disclaimer, the term of this patent is extended or adjusted under 35 U.S.C. 154(b) by 0 days. days.

(21) Appl. No.: 15/178,002

(22) Filed: Jun. 9, 2016

(65) Prior Publication Data

US 2017/0358074 A1    Dec. 14, 2017

(51) Int. Cl.
 *G06T 7/00* (2017.01)
 *G06F 19/10* (2011.01)
 (Continued)

(52) U.S. Cl.
 CPC ............ *G06T 7/0012* (2013.01); *G06F 19/10* (2013.01); *G06F 19/30* (2013.01);
 (Continued)

(58) Field of Classification Search
 CPC ........ G06K 9/0014; G06T 2207/30024; G06T 7/0012; G06T 11/206; G06T 2207/10056;
 (Continued)

(56) References Cited

U.S. PATENT DOCUMENTS 7,801,361 B2  9/2010 Binnig et al. ................. 382/227
8,019,134 B2  9/2011 Athelogou et al. ........... 382/128
(Continued)

FOREIGN PATENT DOCUMENTS

WO  WO 2014/198670  6/2014
WO  WO 2016/034655  9/2015

OTHER PUBLICATIONS

W. Fridman et al., "The immune contexture in human tumours: impact on clinical outcome," Nature Reviews Cancer, vol. 12, No. 4, Jan. 1, 2012, pp. 298-306 XP055023841 ISSN: 1474-175X (10 pages).

(Continued)

*Primary Examiner* — Aklilu Woldemariam
(74) *Attorney, Agent, or Firm* — Imperium Patent Works; Darien K. Wallace

(57) ABSTRACT

An analysis and visualization system analyzes a digital image of a tissue sample. In the sample, cells of a first type are stained in a first way, and cells of a second type are stained in a second way. The system segments the high-resolution image into first and second objects representing cells of the first and second types, respectively. The system also identifies a region of interest, and divides it into tiles. The system generates, for each tile, a first value and a second value. The first and second values for a tile are indicative of densities of the first and second objects in the tile. From the values, a measured correlation coefficient (CC) value is determined. The system compares the measured CC value to a reference CC value, thereby obtaining a correspondence value. The system then displays the image region along with a visualization of the correspondence value.

21 Claims, 14 Drawing Sheets

(51) Int. Cl.
  *G06F 19/00* (2018.01)
  *G06K 9/00* (2006.01)
(52) U.S. Cl.
  CPC ........ *G06K 9/00127* (2013.01); *G06T 7/0026* (2013.01); *G06T 7/0081* (2013.01); *G06K 9/00* (2013.01); *G06T 2207/30096* (2013.01)
(58) Field of Classification Search
  CPC . G06T 2207/10061; G06T 2207/20016; G06T 2207/20021; G06T 2207/20221; G06T 7/33; G06T 7/90; G06T 2207/20081; G06T 7/11; G06T 11/60; G06T 2207/10081; G06T 2207/10084; G06T 2207/10088; G06T 2207/10104; G06T 2207/10108; G06T 2207/30096; G06T 2207/10116; G06T 2207/30004; G06T 2207/30061; G06T 2207/30068; G06T 7/001; G06Q 10/10; G06Q 50/22; G09B 23/28; G01N 15/1459; G01N 15/147; G01N 2021/656; G01N 21/65; G01N 24/082; G01N 33/5005; G01N 33/574; G01N 33/57407; G01N 33/57484; G01N 2800/52; G01N 33/57492; G01N 2333/705; G01N 2333/7051; G01N 2333/70517; G01N 2333/96436; G01N 33/5011; G01N 33/5091; G01N 33/6893; G01N 33/5047; G01N 33/57; G01N 2333/70503; G01N 2333/70532; G01N 33/505; G01N 33/57415; G01N 33/5743; G01N 1/2813; G01N 2001/284; G01N 2001/368; G01R 33/4835; G01R 33/485; G01R 33/5616; A61K 39/39558; A61K 39/395; A61K 2039/505; C07K 2317/21; C07K 16/2818; C07K 2317/76; C12Q 1/6809; C12Q 1/6883; C12N 15/1138; G06F 19/321; G06F 19/3443; G06F 19/3481; G06F 19/3487
  USPC ....... 382/128, 133, 173, 224, 225, 226, 227, 382/158, 195, 305; 345/629, 428; 356/300
  See application file for complete search history.

(56) References Cited

U.S. PATENT DOCUMENTS

| | | | | |
|---|---|---|---|---|
| 8,594,410 B2 | 11/2013 | Schmidt et al. | | 382/132 |
| 8,699,769 B2 | 4/2014 | Schoenmeyer et al. | | G06T 7/0012 |
| 9,042,630 B2 | 5/2015 | Binnig et al. | | G06T 7/0012 |
| 9,298,968 B1 | 3/2016 | Peljto et al. | | G06K 9/00127 |
| 9,741,112 B2* | 8/2017 | Schoenmeyer | | G06T 7/0012 |
| 2002/0186875 A1* | 12/2002 | Burmer | | G06K 9/00127 382/133 |
| 2004/0120557 A1* | 6/2004 | Sabol | | G06Q 10/10 382/128 |
| 2007/0178067 A1* | 8/2007 | Maier | | G01N 21/65 424/93.2 |
| 2008/0292194 A1* | 11/2008 | Schmidt | | G06T 7/0012 382/217 |
| 2009/0215053 A1* | 8/2009 | Galon | | G01N 33/57484 435/6.16 |
| 2010/0103166 A1* | 4/2010 | Warntjes | | A61B 5/055 345/419 |
| 2010/0111396 A1* | 5/2010 | Boucheron | | G06K 9/0014 382/133 |
| 2010/0159497 A1* | 6/2010 | Kimia | | G06T 7/0012 435/29 |
| 2011/0212090 A1* | 9/2011 | Pedersen | | A61K 39/0011 424/133.1 |
| 2012/0112098 A1* | 5/2012 | Hoyt | | B82Y 30/00 250/459.1 |
| 2013/0016886 A1* | 1/2013 | Schoenmeyer | | G06T 7/0012 382/128 |
| 2013/0156279 A1 | 6/2013 | Schoenmeyer et al. | | 382/128 |
| 2013/0249941 A1* | 9/2013 | Shao | | G06F 19/321 345/629 |
| 2013/0330325 A1* | 12/2013 | Grabe | | G01N 33/5011 424/133.1 |
| 2014/0185891 A1* | 7/2014 | Schoenmeyer | | G06T 7/0012 382/128 |
| 2014/0363840 A1* | 12/2014 | Mycek | | G01N 33/5005 435/29 |
| 2015/0049936 A1* | 2/2015 | Tsunomori | | G01N 21/6456 382/133 |
| 2015/0052471 A1* | 2/2015 | Chen | | A61B 6/025 715/771 |
| 2017/0124268 A1* | 5/2017 | Zhang | | G16H 50/20 |

OTHER PUBLICATIONS

Y. Yuan et al., "Quantitative Image Analysis of Cellular Heterogeneity in Breast Tumors Complements Genomic Profiling," Science Translational Medicine, vol. 4, No. 157, 157ra143; Oct. 24, 2012, XP055376527 ISSN: 1946-6234 (10 pages).

European Search Report dated Nov. 6, 2017 by the European Patent Office in the European patent application EP17170141.0 that claims priority to the parent of this application (12 pages).

* cited by examiner

STARTING DIGITAL IMAGE

A PORTION OF THE DIGITAL IMAGE
SHOWN IN EXPANDED FORM

NUMBER CD8 CELLS PER TILE

NUMBER OF PDL1 CELLS PER TILE

DROP DOWN MENU DISPLAYED TO USER

PATHWAY DIAGRAM DISPLAYED TO USER

THE SYSTEM USER ANNOTATES THE DIGITAL IMAGE
TO INDICATE REGIONS A AND B OF INTEREST

NUMBER OF PDL1 CELLS PER TILE IN REGIONS A AND B

DETERMINE THE "MEASURED CC VALUE" FOR REGION A
BY PLOTTING CD8 VS. PDL1 PER TILE COUNTS

DETERMINE THE "MEASURED CC VALUE" FOR REGION B
BY PLOTTING CD8 VS. PDL1 PER TILE COUNTS

VISUALIZATION OF THE MAGNITUDES OF
THE "MEASURED CC VALUES"

|  | MEASURED CC VALUE | REFERENCE CC VALUE | ABSOLUTE VALUE OF DIFFERENCE BETWEEN MEASURED CC VALUE AND THE REFERENCE CC VALUE ($\Delta$CC) |
|---|---|---|---|
| REGION A | -0.303 | +1.0 | +1.3 |
| REGION B | -0.033 | +1.0 | +1.0 |

CALCULATE THE DIFFERENCES BETWEEN THE "MEASURED CC VALUES" AND THE "REFERENCE CC VALUE"

FIG. 15

VISUALIZATION OF THE DIFFERENCES BETWEEN THE "MEASURED CC VALUES" AND THE "REFERENCE CC VALUE" (ΔCC)

VISUALIZATION OF THE MAGNITUDES OF
THE "MEASURED CC VALUES"

VISUALIZATION OF THE DIFFERENCES BETWEEN THE "MEASURED
CC VALUES" AND THE "REFERENCE CC VALUE" (ΔCC)

US 9,990,713 B2

DETECTING AND VISUALIZING CORRELATIONS BETWEEN MEASURED CORRELATION VALUES AND CORRELATION REFERENCE VALUES OF A PATHWAY

TECHNICAL FIELD

The present invention relates to systems and methods for detecting and visualizing correlations between densities of different types of cells in tissue cell samples, and to related systems and methods.

BACKGROUND INFORMATION

The existence of a condition in the human body can often be detected and studied by detecting and studying certain protein-protein or cell-cell interactions that are organized in pathways associated with the condition. An example of an undesirable condition is cancer. As a cancerous tumor grows, the number of cancer cells increases. The human body has means to fight the cancer. Cytotoxic T-cells are a type of immune cells that are able to kill certain cancer cells. Cytotoxic T-cells are frequently present in greater numbers as the number of certain cancer cells increases due to the inflammatory nature of certain cancer types. The relationship between the density of cytotoxic T-cells and the density of such cancer cells can be said to be positively correlated. The actual biochemical communication channels between cells such as immune cells and cancer cells, and within cells such as from cell membrane to the cell nucleus with its DNA, are conceptually organized in pathways and represented in pathway diagrams. In general, multiple proteins in multiple states are involved in a pathway. Protein states may change by phosphorylation, methylation or conformational structure change. Most frequently the biochemical communication may be seen as a signaling pathway in which protein-protein interactions such as binding, or induced state change, are responsible for further processing the signal. Those signals may induce cell death or proliferation, activation of T-cells towards cytotoxic T-cells, or deadly release of toxic substances into the cancer cells by cytotoxic T-cells. Some cancer cells express certain proteins on their membranes that allow them to escape from cytotoxic T-cells and avoid the deadly release of cytotoxic substances by blocking the respective pathway in those T-cells. Drugs may, for example, be administered in an attempt to inhibit a step in a pathway so that another step in the pathway will be inhibited, or will be promoted. A drug may, for example, be administered to fight cancer by increasing the vulnerability of cancer cells to be killed by cytotoxic T-cells. Other drugs may work by causing cancer cells to be recognized as harmful by the immune system. Various drugs may work in various complex ways, and may have complex effects, on various pathways.

In order to study the efficacy of such a drug, it may be desirable to be able to detect changes in particular steps in a particular pathway. If, for example, the ultimate aim of a cancer treatment drug is to increase the vulnerability of cancer cells to be killed by cytotoxic T-cells, then a diagnostic system and tool that allows a physician or researcher to spatially measure the density of cytotoxic T-cells around cancer cells, which indicates specific immune-escape membrane proteins, would be useful. More generally, a diagnostic system and tool that allows a researcher to study relationships between any desired pair of proteins in a pathway would be useful in the development of medical treatments, drugs and diagnostics.

SUMMARY

A pathway protein correlation value determining and visualization system, in one embodiment, involves a server and a network-connected computer. A high-resolution digital image of a tissue sample is loaded into the system. There are various ways that the digital image can be obtained. In one example, a tissue sample is taken from a patient (for example, a cancer patient) and put on a slide for dual staining. The tissue slice on the slide is stained with a first antibody stain that is specific to a first protein present in a first type of cells, for example, CD8-positive cytotoxic T-cells. The tissue slice is stained with a second antibody stain that is specific to a second protein present in a second type of cells, for example, PDL1-positive cancer cells. A high-resolution Whole-Slide-Image (WSI) is taken of the slide. The resulting high-resolution digital image is the Whole-Slide-Image that is loaded into the system.

After the WSI has been loaded into the system, the system segments the digital image into first image objects representing cells of the first type and into second image objects representing cells of the second type. The system then identifies a "reference correlation coefficient (CC) value". In one example, the system identifies the reference CC value by displaying a diagram of a pathway to the system user. The pathway diagram is displayed on the display of the network-connected computer. Individual proteins in the pathway may be presented in the form of individual user-selectable icons. The user uses the network-connected computer to select two proteins of interest. From this user selection, the system identifies a corresponding, previously stored, reference correlation coefficient (CC) value that pertains to the two proteins. The reference CC value may indicate a positive correlation, a negative correlation, or no correlation (neutral correlation).

The system also identifies an image region in the digital image. In one example, the system identifies the image region by prompting the user to use the network-connected computer to annotate the digital image. In response, the user annotates the digital image, thereby indicating a certain part of the image data to be the image region. The system divides this image region into a set of tiles. The system generates, for each tile, a first value and a second value. The first value is indicative of the density of the first image objects in the tile. The second value is indicative of the density of the second image objects in the tile. After a pair of these values (the first value and the second value) has been generated for each tile, the system uses the pairs of values to determine a measured correlation coefficient (CC) value. In one example, a Spearman rank correlation coefficient determining routine is used to generate a Spearman correlation coefficient (CC) value between the first value and the second value. This Spearman CC value that is output from the routine is considered to be the "measured CC value".

The system then compares the "measured CC value" to the "reference CC value", thereby generating a "correspondence value". The correspondence value indicates the degree to which the measured CC value matches the reference CC value. In one example, the correspondence value is the absolute value of the difference between the measured CC value and the reference CC value.

The system then displays the image region along with a visualization of the correspondence value for the image region. In one example, the visualization of the correspondence value is a shading of the image region, where the degree of shading indicates the magnitude of the correspondence value. In one example, a darker shading indicates a better match between the measured CC value and the reference CC value, whereas a lighter shading indicates a poorer match between the measured CC value and the reference CC value. A key is displayed along with the shaded image. The key indicates, for each possible shade of the image region, the corresponding correspondence value.

Further details and embodiments and methods are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 15 is a diagram that shows how the differences between the measured CC values and the reference CC value are determined.

DETAILED DESCRIPTION

Reference will now be made in detail to some embodiments of the invention, examples of which are illustrated in the accompanying drawings.

Figure 1:
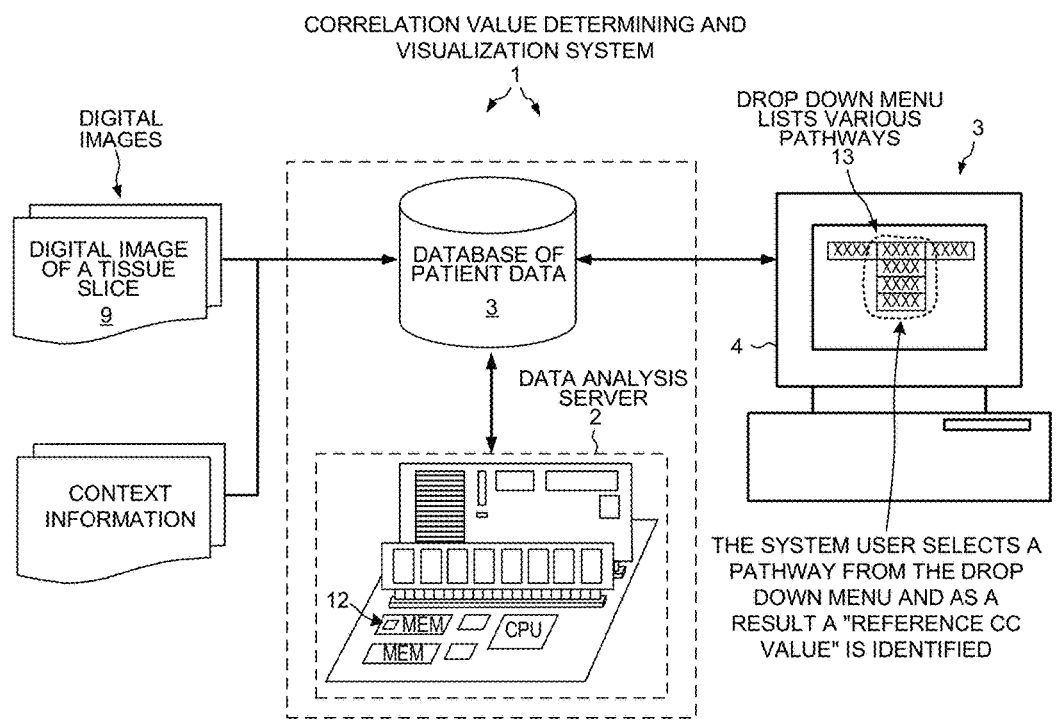
FIG. 1 is a diagram of a pathway cell type correlation value determining and visualization system.

FIG. 1 is a conceptual diagram of a system 1 for analyzing stained slices of tissue of a patient, for determining correlations between structures of different types in that tissue, and for displaying visualizations of differences between measured correlation values and reference correlation values. System 1 includes a data analysis server 2 and a network-connected computer 3. Image analysis software 12 of the system is stored in a non-transitory manner on a computer-readable medium (for example, semiconductor memory and/or on a magnetic hard disc) in the server 2. The data analysis server 2 maintains and stores a database 3 of case files of patient data. A physician or laboratory person or other health care professional can use the network-connected computer 3 to interact with system 1, to cause data including digital image data to be loaded into the system, to cause the system to perform various types of analyses on the data, and to view analysis result information. The analysis result information may, for example, be viewed on the display 4 of the computer 3. The display 4 in this case is a computer monitor.

Figure 2:
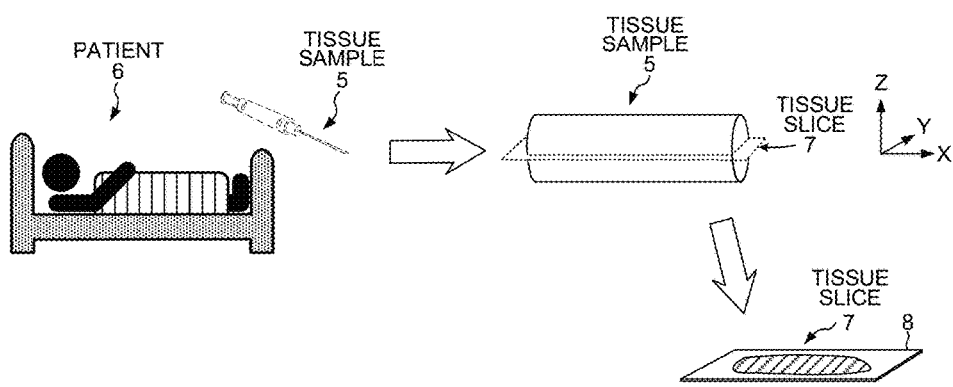
FIG. 2 illustrates an example of how a digital image, to be supplied as in an input to the system of FIG. 1, is generated.

FIG. 2 illustrates how, in the present example, a sample 5 of cancerous tissue is taken from the lung of a cancer patient 6. The cancer type is NSCLC (non-small-cell lung carcinoma). A very thin slice 7 of the sample is made. The slice 7 is placed on a microscope slide 8 and stained with two biomarkers. This is referred to as a "double stain" or "duplex staining". In the present example, the first biomarker of the double stain is a CD8 antibody stain that stains cytotoxic T-cells (also referred to here as "immune cells") to have a magenta color. When the level of CD8 expression for a membrane of a cell, indicated by anti CD8 stain, exceeds a certain level, then the cell is regarded as CD8-positive (CD8+). The second biomarker of the double stain is a PDL1 antibody stain that stains certain PDL1-positive tumor cells (also referred to here as "cancer cells") so that these tumor cells have a brown color. When the level of PDL1 expression for the membrane of a cell, indicated by anti PDL1 stain, exceeds a certain level, then the cell is regarded as PDL1-positive (PDL1+). A high resolution color digital image 9 is then taken of the stained slice.

Figure 3:
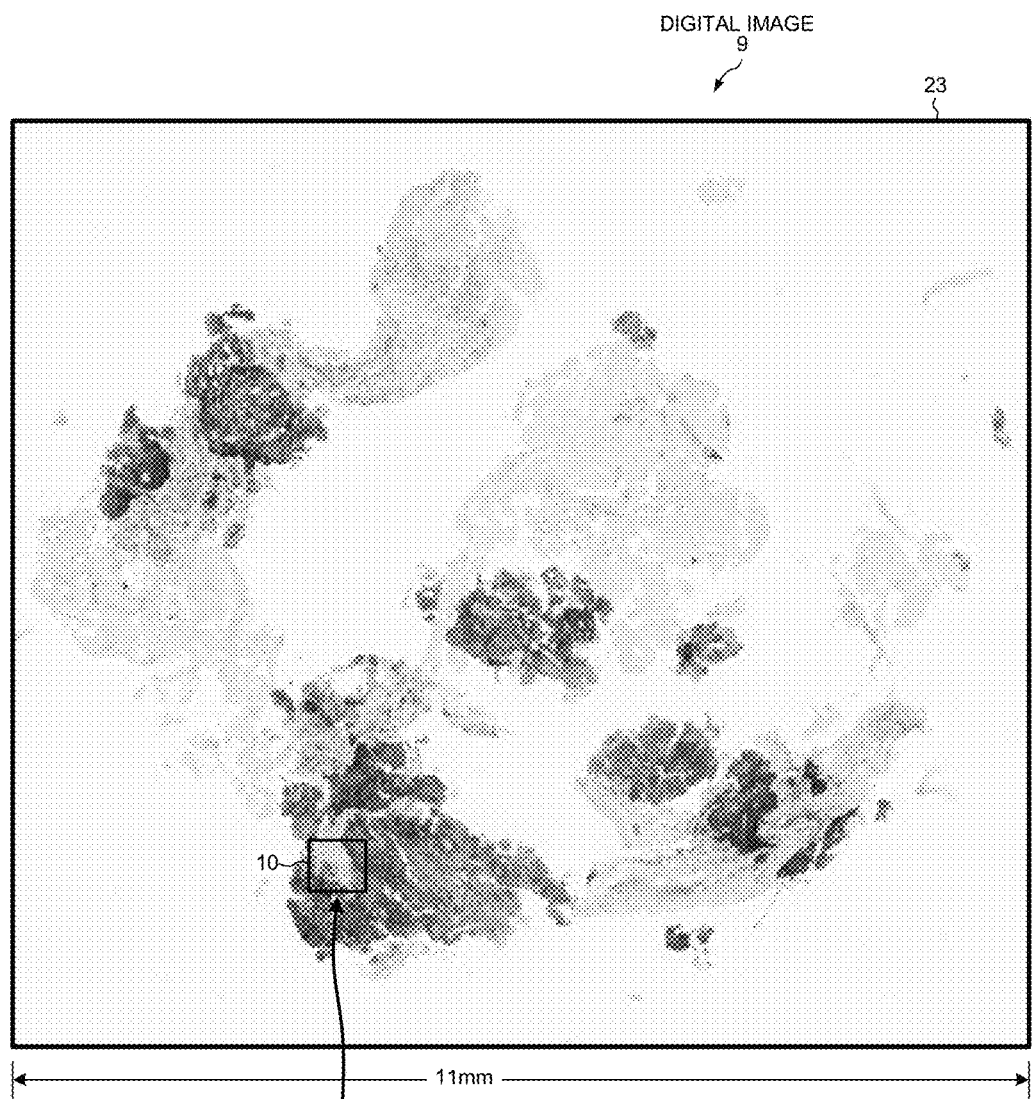
FIG. 3 is a grayscale version of the digital image.

FIG. 3 is a grayscale version of the digital image 9.

Figure 4:
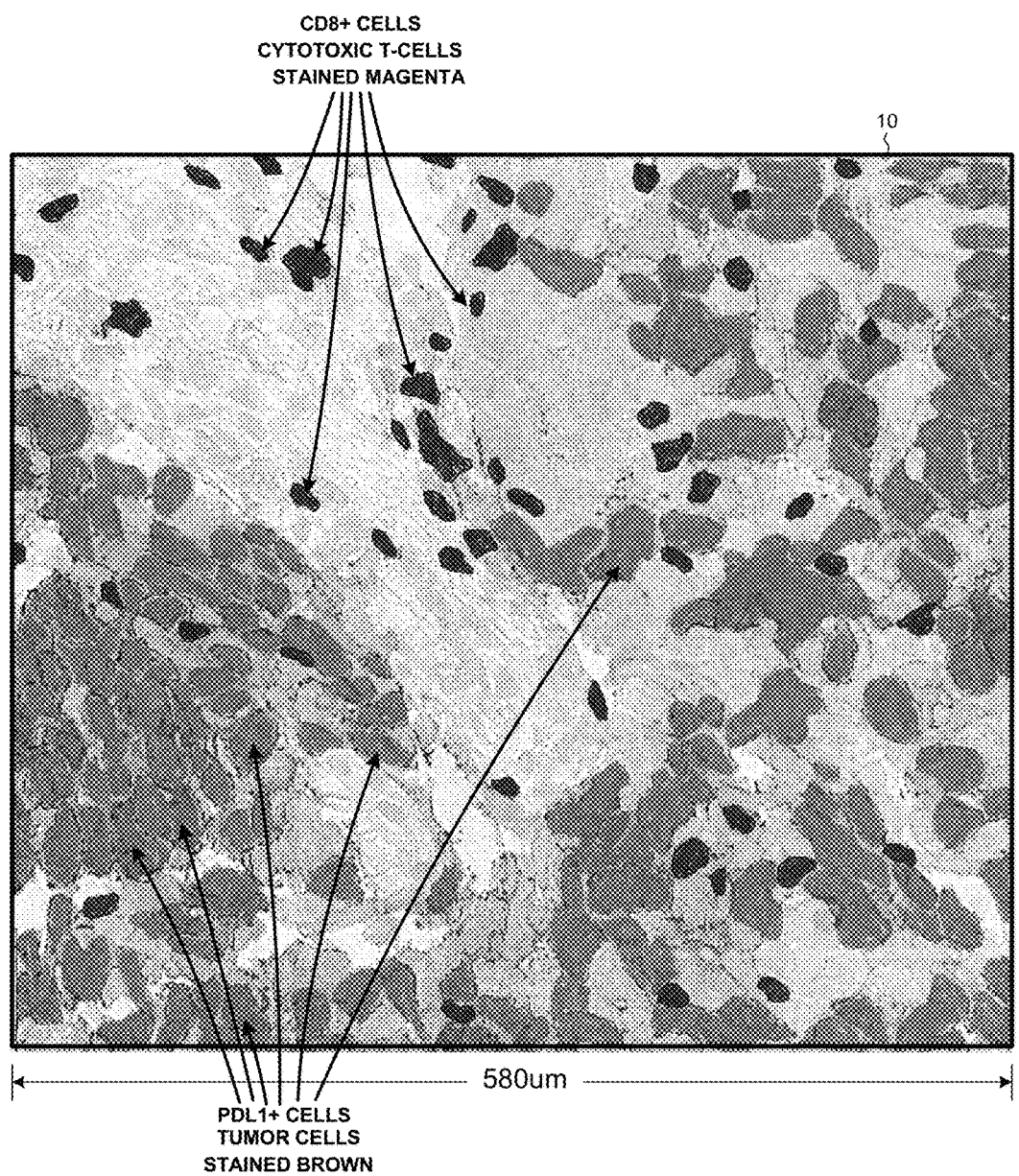
FIG. 4 is portion of the digital image of FIG. 3.

FIG. 4 shows the portion 10 of the digital image 9 of FIG. 3 in expanded form. The digital image 9 is loaded into system 1 and is stored in database 3 in the case file for the patient 6. Metadata is stored along with the digital image 9. The metadata includes information about the digital image including: 1) an identification of the patient, 2) the type of tissue, 3) the resolution of the digital image, 3) the creation date of digital image, and 4) information indicating what the particular stains with which the tissue sample had been stained.

When the digital image 9 and its associated metadata is loaded into the system, the system reads the metadata. From the metadata, the system automatically determines what kinds of analyses the system can perform on the digital image. In the example of the digital image 9 of FIG. 3 being stained with the CD8 antibody stain and the PDL1 antibody stain, and in the example of FIG. 3 in which the tissue is lung cancer tissue, the system determines that it can perform a cell counting operation for CD8+ and PDL1+ cells (immune cells and cancer cells) so that the user can then view pathway correlation coefficient information as further described below. From the type of analysis to be done on the digital image, the system chooses the rule-sets to use in identifying cells in the digital image. Each rule-set has process steps that apply an algorithm based on a membership function to objects formed from linked pixels. In the present example, the rule sets, membership functions, algorithms and filters are used to perform the appropriate segmentation and classification operations on the digital image such that individual immune cells in the digital image are identified and such that individual cancer cells in the digital image are identified. In one example, a first segmentation process is performed on the pixel data of the digital image. This first segmentation process searches for pixels whose colors fall with a selected color range and whose pixel locations in the image are such that they form a shape of a first type of cell component. In this case, the first type of cell component is a cell membrane. For each identified cell component of the first type, a corresponding object is created in a hierarchical object data network. A second segmentation process is performed on the pixel data of the digital image. This second process searches for pixels whose colors fall within a selected color range and whose pixel locations in the image are such that they form a shape of a second type of cell component. In this case, the second type of cell component is a cell nucleus. For each identified cell component of the second type, an object is created in the hierarchical data network. First and second objects are then classified according to the membership functions. As a result of the classification, selected first and second objects are linked as associated with a higher level "immune cell" object in the data network. In one example, an object corresponding to a cell membrane is linked to an object corresponding to the nucleus of the same cell. In this way, a higher level "immune cell object" is created for each immune cell pictured in the digital image. Each higher level immune cell object indicates the pixel locations in the digital image 9 that are associated with the immune cell.

This same process is performed with different rule sets appropriate for identification of cancer cells. A higher level "cancer cell object" is created for each cancer cell detected in the digital image. Each higher level cancer cell object indicates the pixel locations in the digital image 9 that are associated with the cancer cell.

For additional information on the methodology of how cells can be identified in a digital image, see the following documents: 1) U.S. Pat. No. 7,801,361, 2) U.S. Pat. No. 8,019,134, 3) U.S. Pat. No. 8,594,410, and 4) U.S. Pat. No. 9,042,630 (the entire subject matter of each of these patents is incorporated herein by reference).

Figure 5:
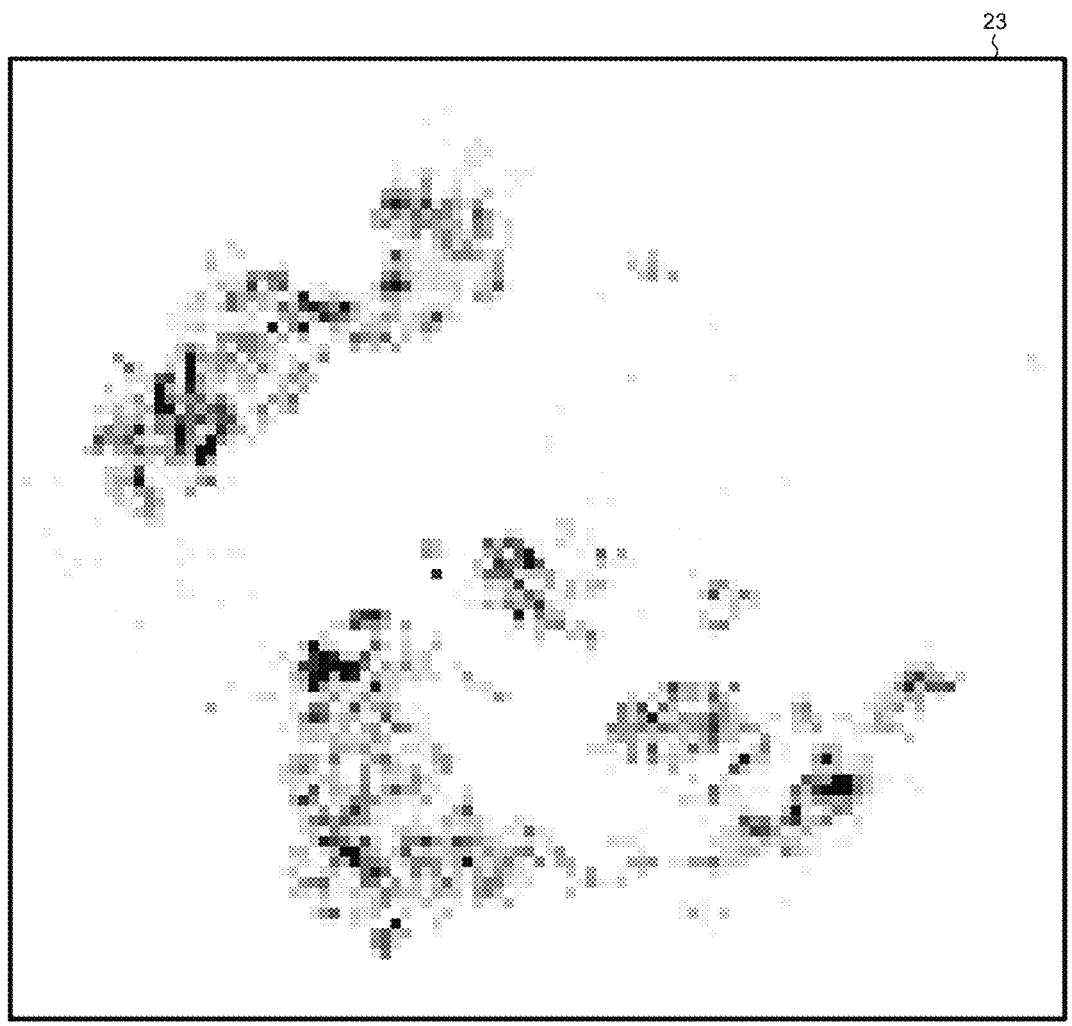
FIG. 5 is a diagram that illustrates the number of identified CD8-positive immune cells (first cell type) in each tile of the digital image.

Next, system 1 divides the digital image 9 into a two-dimensional matrix of tiles. System 1 counts the number of immune cells identified in each tile, thereby obtaining an immune cell count value. FIG. 5 is a diagram that illustrates the number of identified immune cells in each tile. In the diagram of FIG. 5, each tile is shaded with a shade that indicates the immune cell count value. A key 11 indicating the immune cell count indicated by each shade is illustrated below the image.

Figure 6:
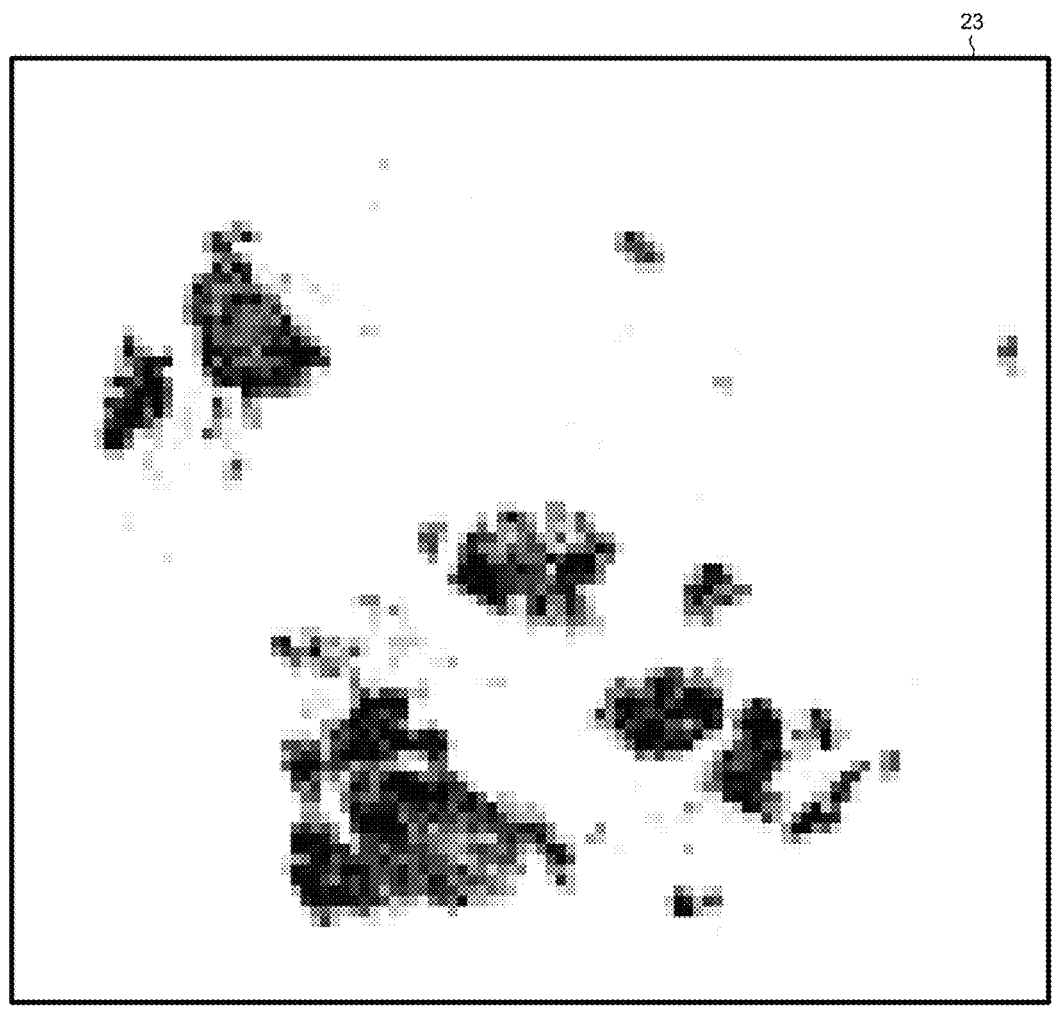
FIG. 6 is a diagram that illustrates the number of identified PDL1-positive cancer cells (second cell type) in each tile of the digital image.
Figure 6:
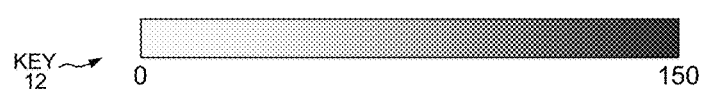

Likewise, system 1 counts the number of identified cancer cells in each tile, thereby obtaining a cancer cell count value for each tile. FIG. 6 is a diagram that illustrates the number of identified cancer cells in each tile. Each tile in FIG. 6 is shaded with a shade that indicates the cancer cell count value. A key 12 indicating the cancer cell count indicated by each shade is illustrated below the image. Accordingly, for each tile, there is an immune cell count value and the cancer cell count value. This pair of cell count values for each tile of the digital image is stored by system 1 in association with the digital image 9 in the case file for the patient in the database 3. The processing described above is a sort of pre-processing that is performed before the user uses the system 1 to visualize correlations attendant in the digital image. The pre-processing results are stored in association with the digital image 9 in the case file of the patient.

Figure 7:
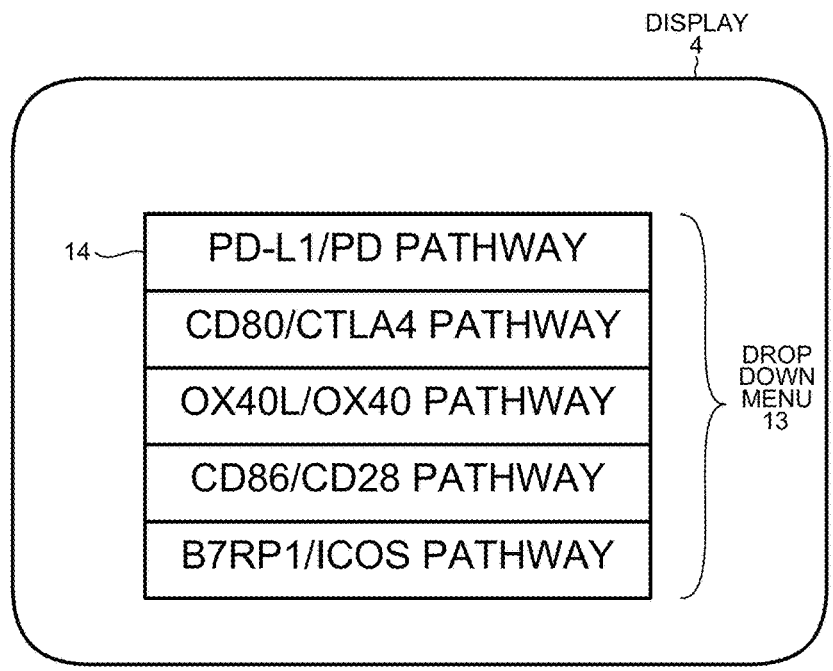
FIG. 7 is a drop down menu that is displayed to the user of the system.

To use system 1 to visualize correlations, the user uses computer 3 to select the case file of the patient. In response to this selection, the system 1 displays a list of the digital image files in the case file. This display of a digital image file may, for example, be a display of the file name of the digital image. From this displayed list, the user uses computer 3 to select the digital image file for the digital image 9 of FIG. 3. In response, the system 1 displays a drop down menu 13 on display 4 of computer 3. The drop down menu 13 presents a list of pathways, where in the individual pathways in the list are displayed and represented by user-selectable icons. FIG. 7 is a diagram of the drop down menu 13 presented to the user. The user clicks on one of the user-selectable icons 14 of the drop down menu and thereby selects one of the pathways.

Figure 8:
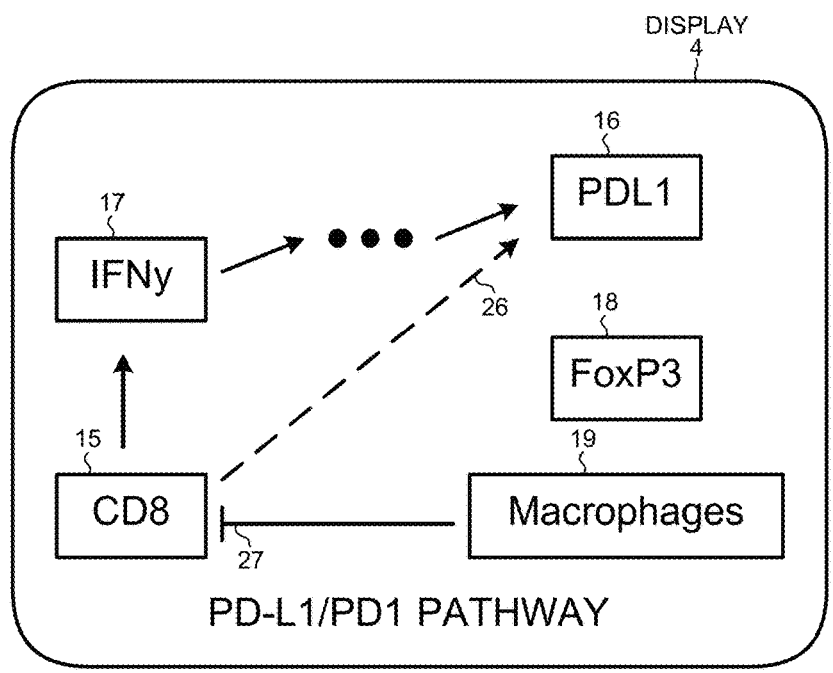
FIG. 8 is a pathway diagram that is displayed to the user of the system.

In response to the user selection of a pathway, the system 1 displays to the user on the computer display 4 a pathway diagram for the selected pathway. FIG. 8 is a pathway diagram for the pathway selected by the user when the user clicked on the icon 14 in the FIG. 7. The pathway diagram includes a number of user-selectable icons 15-19. In the pathway diagram, one of the icons 15 is labeled CD8. Another of the icons 16 is labeled PDL1. As is known in the art, an arrow symbol such as 26 indicates an activation (positive correlation). In the case of arrow 26, the correlation is positive in that an increase in the density of CD8+ cells will result in a commensurate increase in the density of PDL1+ cells. As is known in the art, a dead-end symbol such as dead-end symbol 27 indicates an inhibition (negative correlation). In the case of dead-end symbol 27, the correlation is negative in that an increase in the density of macrophages will result in a commensurate decrease in the density of CD8+ cells.

The user clicks on the two icons 15 and 16 in order to be shown result information about the relationship between CD8+ cells and PDL1+ cells. The border of a selected icon may, for example, appear darker and thicker in order to indicate to the user that the icon has been selected. In response to this user input information, the system 1 looks up a "reference correlation coefficient value" (reference CC value) for CD8+ cells versus PDL1+ cells. The "reference CC value" is a known reference value that has been previously loaded into the system. In the present example, a reference CC value has a value that is either −1, 0 or +1. In the case of the CD8-to-PDL1 "reference CC value" for the pathway displayed in FIG. 8, the "reference CC value" is +1. The system 1 identifies this reference CC value in response to the user's selection of icons 15 and 16 of the pathway diagram.

Figure 9:
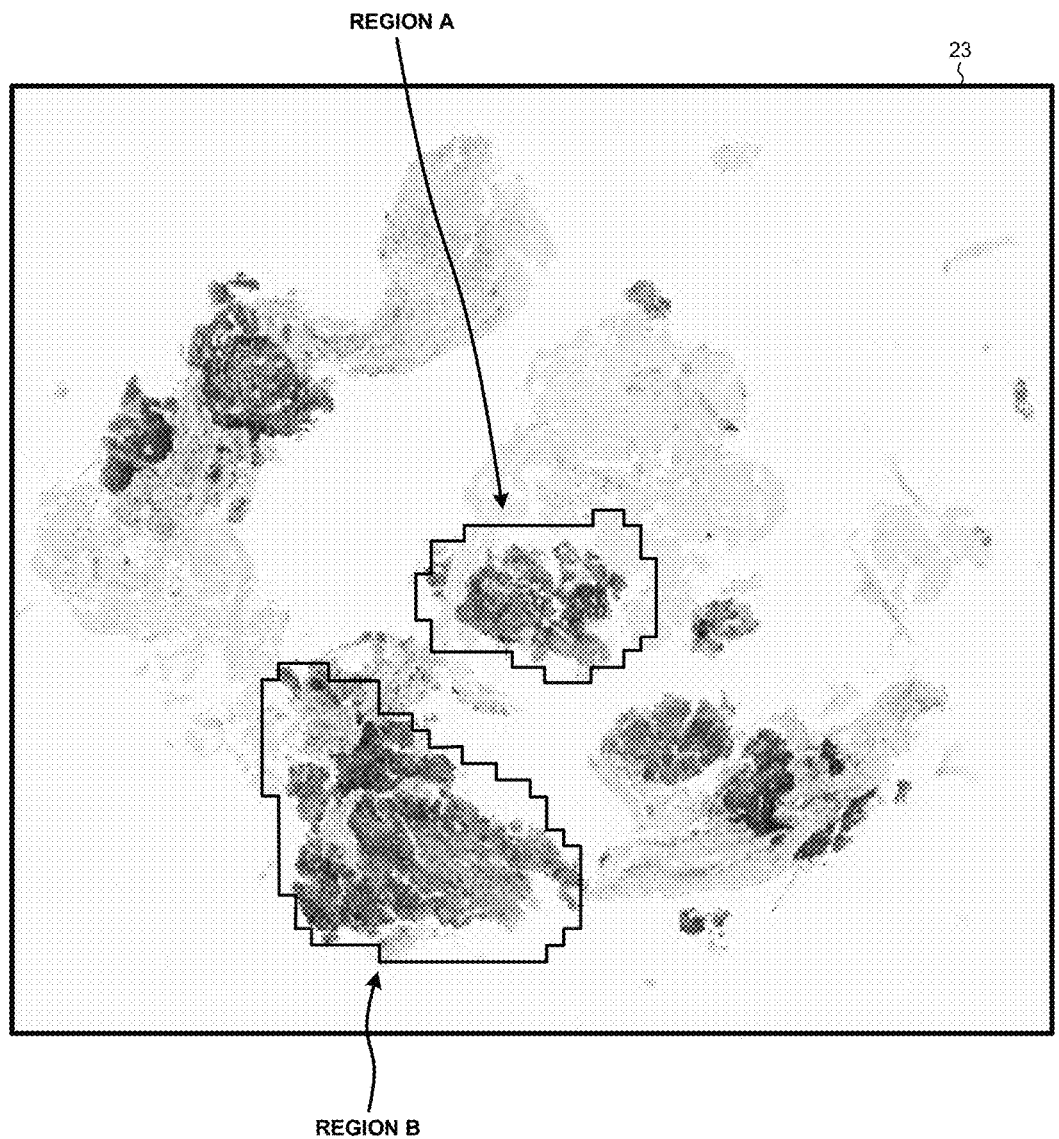
FIG. 9 is a diagram of the digital image after the user has annotated the digital image to identify regions of interest.

System 1 also prompts the user to use the computer 3 to annotate the digital image 9 in order to identify one or more image regions of interest. The user responds by using the computer 3 to enter the annotation information that defines one or more image regions. The user may, for example, use the computer's mouse to scribe a loop around a portion of the digital image 9 that is of interest to the user. FIG. 9 illustrates the digital image 9 after it has been annotated by the user to identify an image region of interest A and an image region of interest B. System 1 uses the annotation information to identify the cell count information for tiles of each of the two regions A and B. From this point on in the process, cell count information for tiles outside image regions A and B is ignored.

Figure 10:
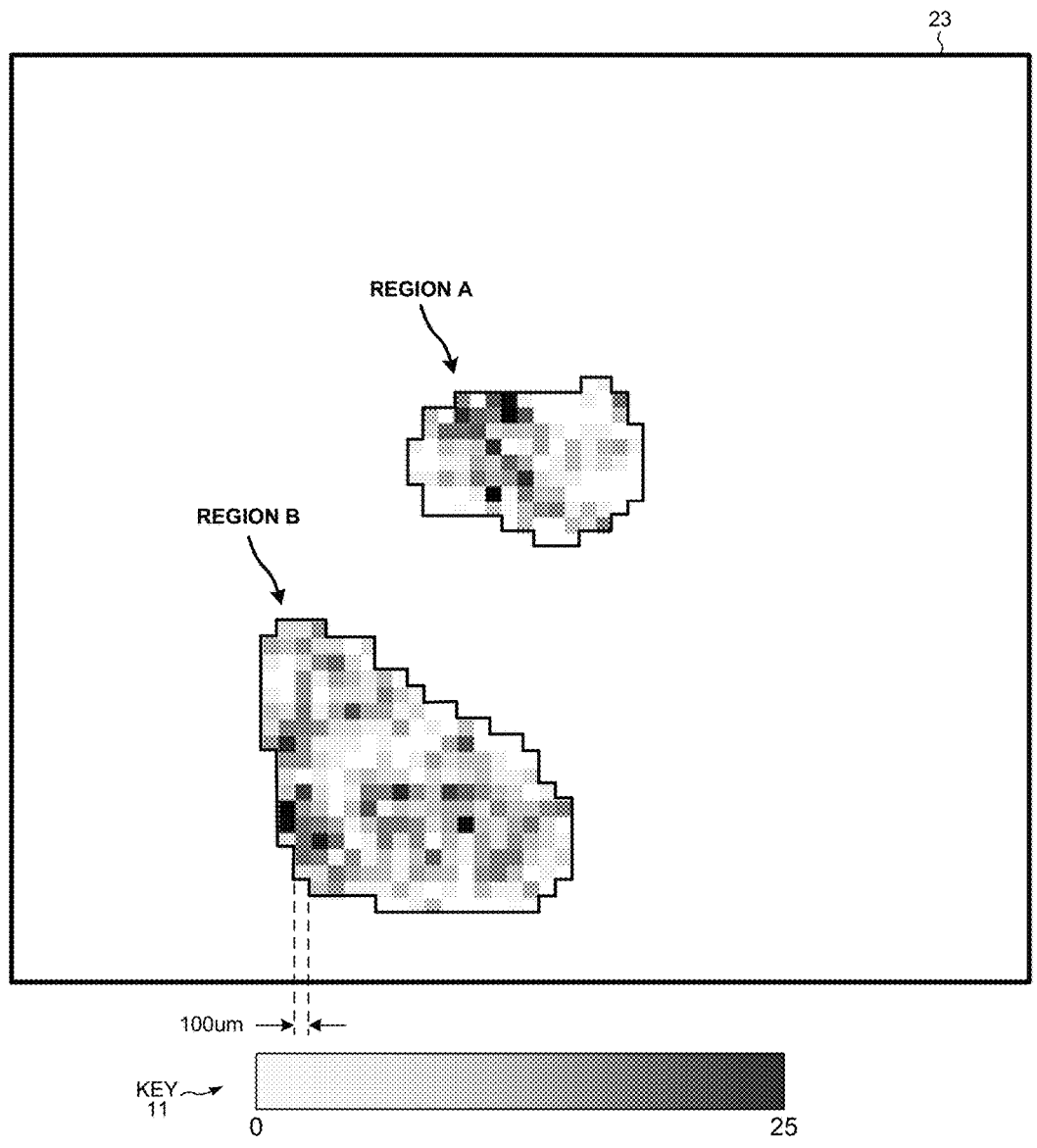
FIG. 10 is a diagram that indicates the number of CD8-positive immune cells (first cell type) per tile in the regions A and B of interest.

FIG. 10 shows the immune cell count information (CD8+ cell count information) after count information for tiles outside of the regions A and B has been excluded.

Figure 11:
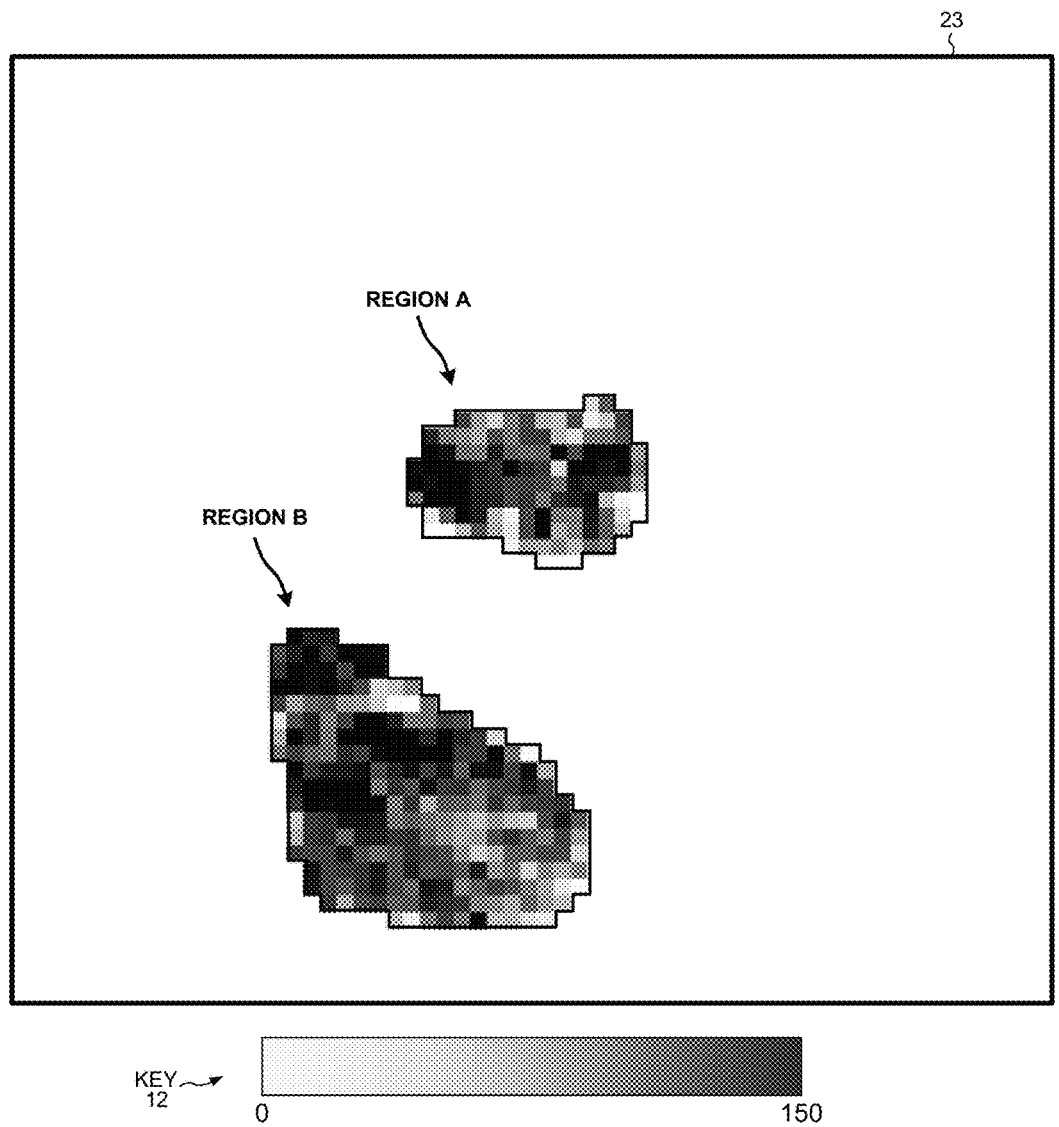
FIG. 11 is a diagram that indicates the number of PDL1-positive cancer cells (second cell type) per tile in the regions A and B of interest.

FIG. 11 shows the cancer cell count information (PDL1+ cell count information) after count information for tiles outside of the regions A and B has been excluded.

Figure 12:
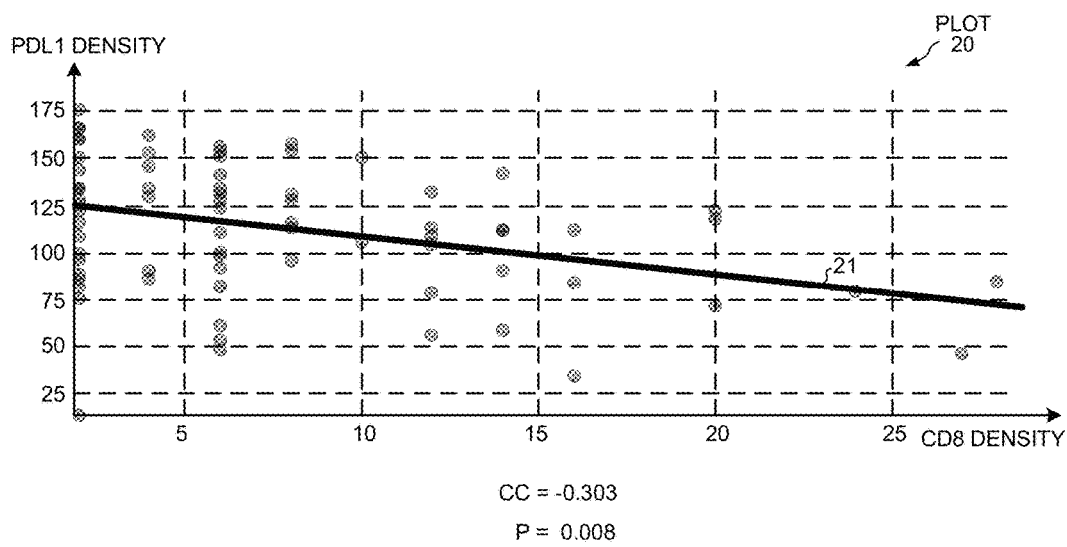
FIG. 12 is a scatter plot illustration of how the measured CC value for region A of interest is determined.

For region A, each tile has an immune cell count value (a count of the CD8+ number of cells) and a cancer cell count value (a count of PDL1+ number of cells). For each tile in the region of interest, a dot representing these two cell count values is plotted on a two-dimensional scatter plot 20 as shown in FIG. 12. On the vertical axis is the PDL1+ cell density (PDL1 density). This PDL1 density is the same as the tumor cell count in the tile because all the tiles are of the same size. On the horizontal axis is the CD8+ cell density (CD8 density). This CD8 density is the same as the immune cell count in the tile because all the tiles are of the same size. The pair of count values for each dot is used to place the dot in the scatter plot of FIG. 12. There is one dot for each tile.

After a dot for each of the tiles of region A has been marked on the scatter plot, the system 1 determines a line 21 that passes through the dots. The line 21 is the line that has a best fit (according to a particular metric or rule) to the dots. There are techniques known in the numerical analysis arts that can be employed to determine line 21. In one example, system 1 employs a Spearman rank correlation coefficient determining numerical analysis routine. The output of the Spearman rank correlation coefficient routine is a "correlation coefficient" (CC) value and a probability value (P value). The CC value is referred to here as the "measured CC value" because it is determined from the data of the digital image. The measured CC value indicates and quantifies the strength of the detected relationship between the density of CD8+ cells of tiles in a region versus the density of PDL1+ cells of tiles in the same region. A positive "measured CC value" indicates that there is a positive correlation of PDL1+ cell density and CD8+ cell density. Namely, as the number of CD8+ cells per tile increases along the x axis of the plot 20, the number of PDL1+ cells per tile in the y axis is also seen to increase. The number of CD8+ cells in a tile is therefore said to be positively correlated to the number of PDL1 stained cells per tile. A negative "measured CC value" indicates that there is a negative correlation of the PDL1+ cell density versus the CD8+ cell density. If the number of CD8+ cells in a tile along the x axis of plot 20 increases, then the number of PDL1+ cells in the tile as plotted on y axis should decrease. A "measured CC value" near zero indicates that increasing or decreasing the number of CD8+ cells in a tile does not tend to change the number of PDL1+ cells per tile. In the example of region A, the plot and analysis of FIG. 12 indicates that the "measured CC value" is −0.303.

The probability value P as output by the Spearman rank correlation coefficient determining routine is 0.008. The probability value represents the probability that the detected correlation happened by chance. The scale of the probability value is in a range from 0 to 1. A lower probability value indicates that the determined correlation value is less likely to be a result of chance. A higher probability value indicates that the determined correlation value is more likely to be a result of chance.

Figure 13:
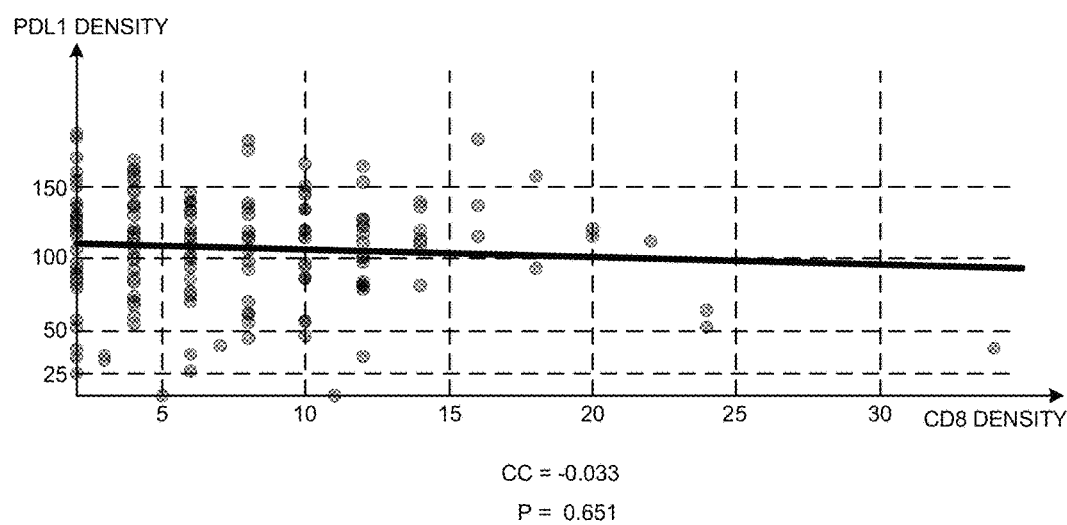
FIG. 13 is a scatter plot illustration of how the measured CC value for region B of interest is determined.

FIG. 13 shows how the same correlation coefficient determining process is carried out for the other region of interest, region B. As indicated in FIG. 13, the "measured CC value" for region B is −0.033, and the probability value is 0.651. Accordingly, for each region of interest, the system 1 determines a "measured CC value" and a "P value". This pair of values, for each region of interest, may be displayed on the display 4 of the computer 3.

Figure 14:
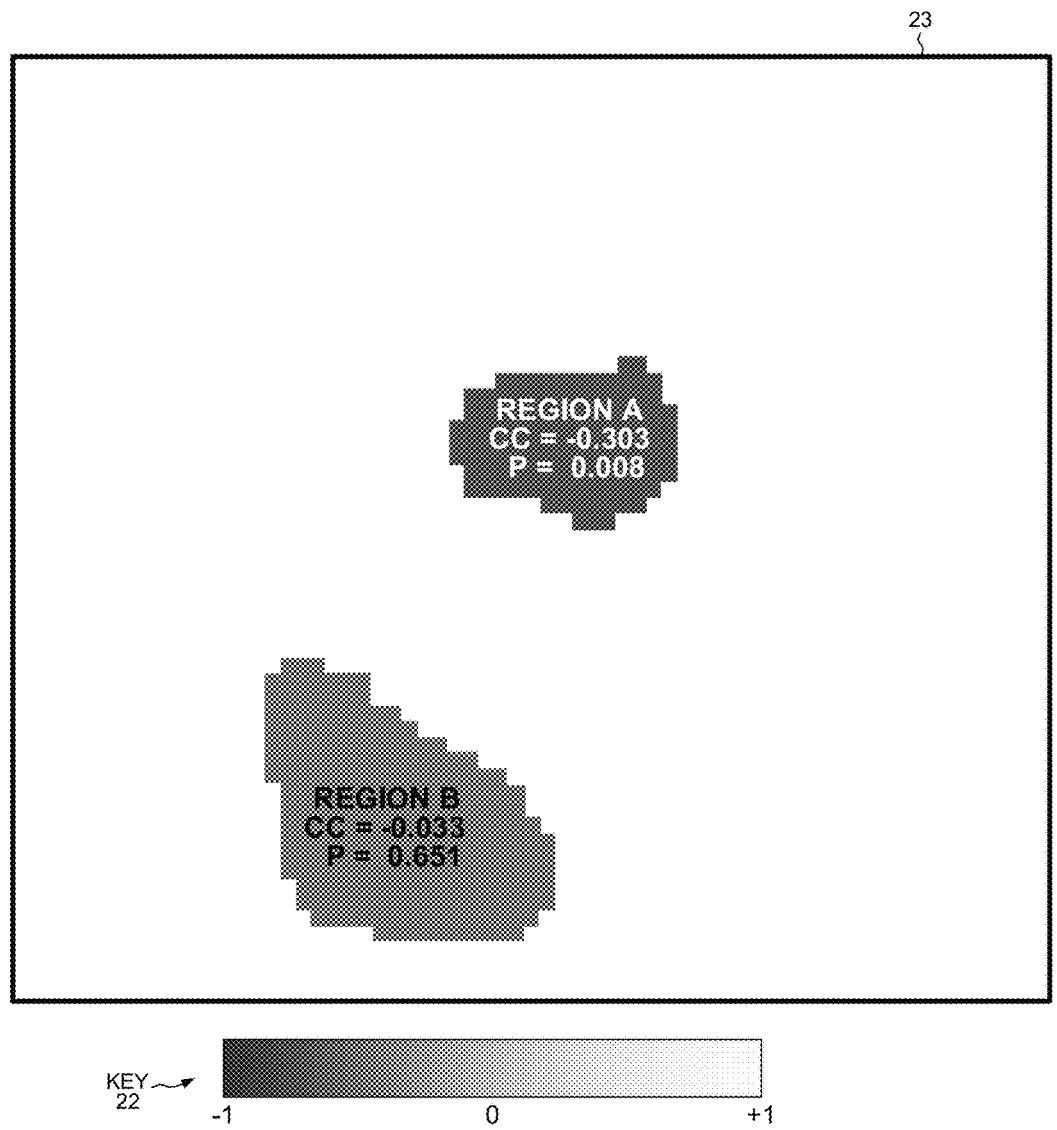
FIG. 14 is a diagram of the visualization of the magnitudes of the measured CC values for regions A and B.

In FIG. 14, the magnitude of the "measured CC value" for each region of interest, on a scale of from −1 to +1, is graphically illustrated and displayed to the user by shading the region of interest. The shading of a region indicates the magnitude of the measured CC value of the region. A key 22 indicating the "measured CC value" indicated by each shade is illustrated below the displayed image. The rectangular boundary 23 of the image of FIG. 14 represents the same region of the digital image information as the rectangular boundary 23 in the images of FIGS. 3, 5, 6, 9, 10 and 11.

Next, for each region of interest, the system 1 compares the "measured CC value" with the "reference CC value". As explained above, the "reference CC value" is a value that is identified by the system 1 as a result of the user's identification of the CD8 and PDL1 icons in the displayed pathway diagram of FIG. 8. In the specific example, the system 1 does the comparison for a region of interest by determining the absolute value of the difference between the "measured CC value" of the region and the "reference CC value".

FIG. 15 is an illustration of how the system determines the absolute values of differences for regions A and B. For region A, the "measured CC value" is −0.303, and the "reference CC value" is +1.0, so the absolute value of the difference ($\Delta$CC) between these two CC values is +1.3. For region B, the measured CC value is −0.033, and the reference CC value is +1.0, so the absolute value of the difference ($\Delta$CC) between these two CC values is +1.0.

Figure 16:
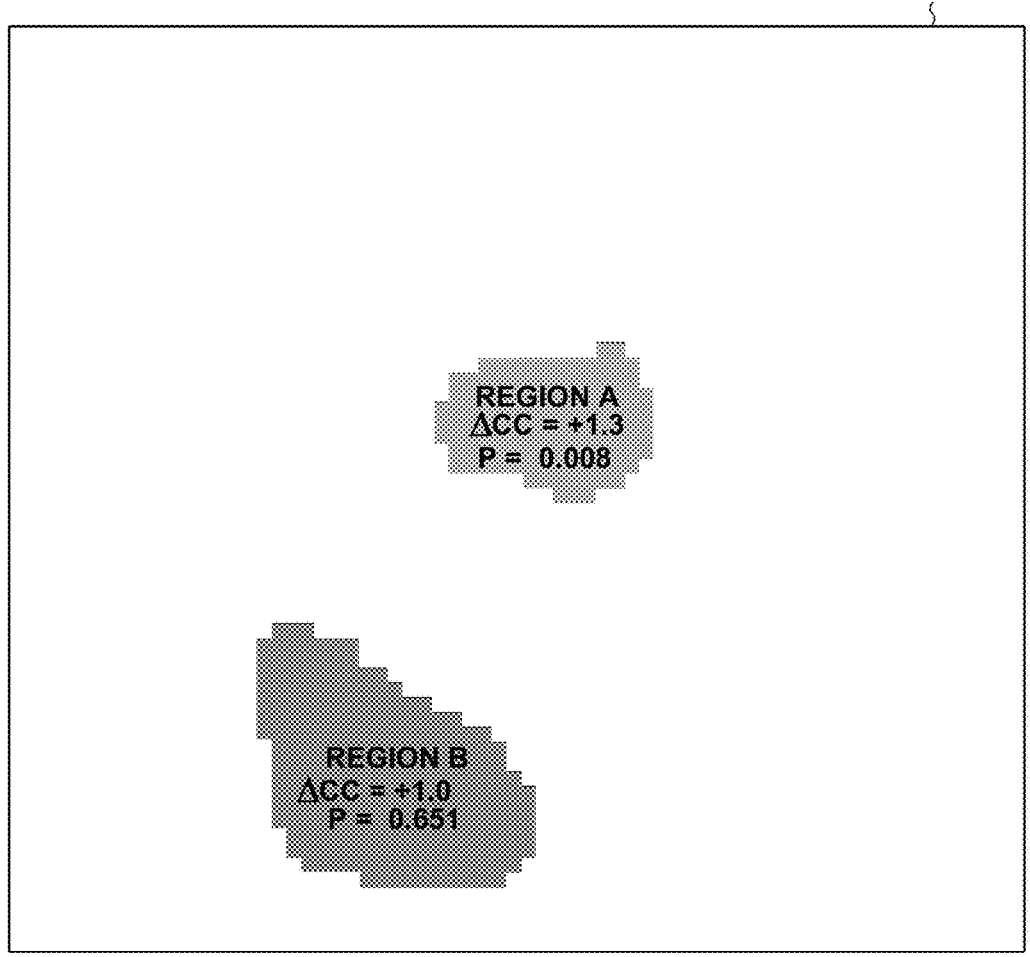
FIG. 16 is a diagram of the visualization, as presented by the system to the user, of the differences between the measured CC values and the reference CC value.
Figure 16:
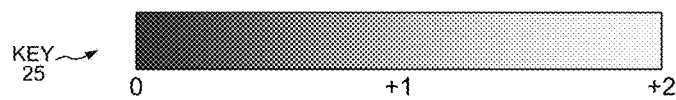

FIG. 16 is an illustration of how a visual indication of the $\Delta$CC values of FIG. 15 is displayed on display 4 to the system user. The area of the digital image is displayed, but areas of the digital image outside the regions of interest are shown with a background color and shading. Each region of interest is shaded with a shading that indicates the absolute value for that region. A key 25 indicating the magnitude of the difference value on a scale from 0 to +2 is illustrated below the image. This key indicates, for each possible shading of a region of interest, what the corresponding $\Delta$CC difference value is. In the illustrated example, region A has a shading indicating that the $\Delta$CC difference value is +1.3. Region B has a shading indicating that the $\Delta$CC difference value is +1.0. In addition to the shading, the $\Delta$CC difference value is also indicated in text as a textual overlay to the region. For example, the text "$\Delta$CC=+1.3" appears as a textual overlay over the region A, and the text "$\Delta$CC=+1.0" appears as a textual overlay in the region B. In addition to the textual indications of the $\Delta$CC difference values, a textual indication of the P value of each region is also presented as an overlay on the corresponding region. For example, the text "P=0.008" appears in region A, and the text "P=0.651" appears in region B.

In the embodiment described above in connection with FIGS. 1-16, system 1 identifies two regions of interest A and B by soliciting and receiving annotation input information from the user. In a second embodiment, system 1 identifies regions of interest automatically itself by sectioning the image boundary area 23 of the overall digital image 9 into a two-dimensional array of larger tiles. Each of these larger tiles is a region of interest. In one example, each larger tile is ten times wider than one of the smaller tiles in which cells are counted, and is ten times taller than one of the smaller tiles in which cells are counted. The analysis method performed by system 1 is the same as in the embodiment described above in connection with FIG. 1-16, except that in the second embodiment each of these larger tiles is treated as a discrete region of interest. Accordingly, a "measured CC value" is determined for each larger tile.

Figure 17:
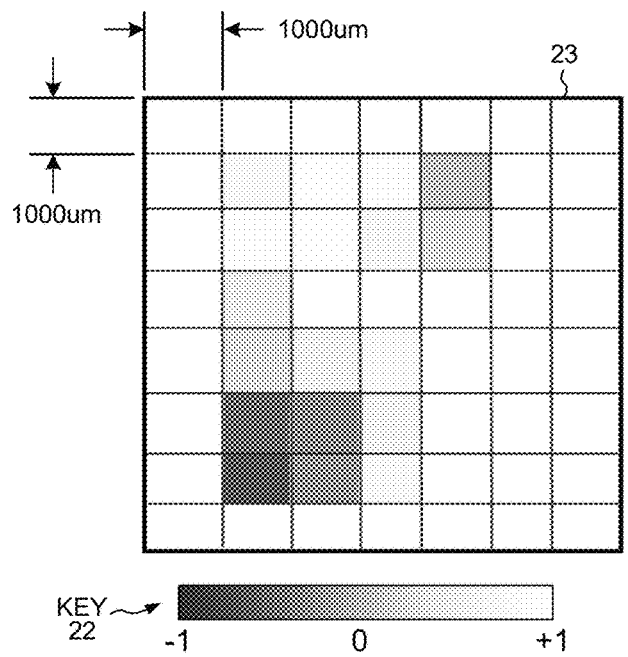
FIG. 17 is a diagram that shows the visualization, as presented by the system to the user, of the magnitudes of the measured CC values of the regions of interest, in accordance with a second embodiment.

FIG. 17 is a diagram showing each of these larger tiles appropriately shaded in accordance with the visualization step illustrated in FIG. 14. The degree of shading of a larger tile indicates the magnitude of the measured CC value of the larger tile. Shading key 22 of FIG. 17 is the same shading key as key 22 of FIG. 14.

Figure 18:
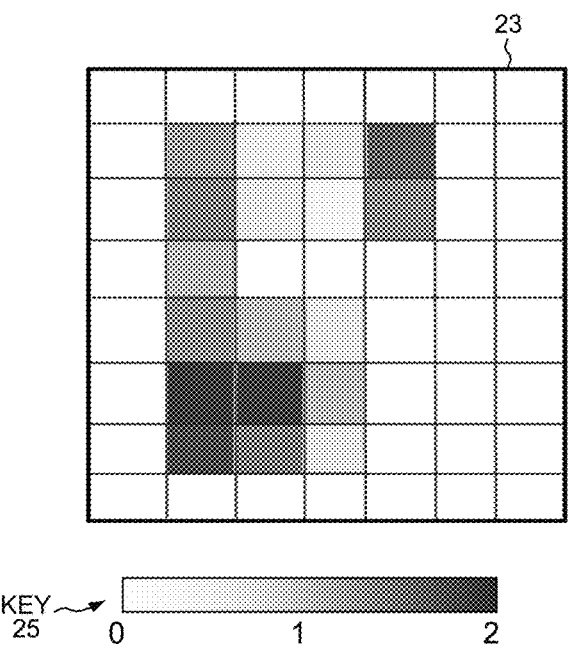
FIG. 18 is a diagram that shows the visualization, as presented by the system to the user, of the differences between the measured CC values of the regions of interest and the reference CC value, in accordance with the second embodiment.

FIG. 18 is a diagram that shows the subsequent step of visualizing the differences between the measured CC values of the larger tiles and the reference CC value. For each larger tile (a region of interest), the absolute value of the difference between the measured CC value of the larger tile and the reference CC value is determined. The degree of shading of a larger tile indicates the magnitude of the difference between the measured CC value of the larger tile and the reference CC value. Shading key 25 of FIG. 18 is the same shading key as key 25 of FIG. 16.

Although the present invention has been described in connection with certain specific embodiments for instructional purposes, the present invention is not limited thereto. In the example described above, a single tissue slice 7 was double stained, and a high-resolution digital photograph of this slice was taken in order to obtain the starting digital image 9 that is processed in the method described above. In another example, there are multiple tissues slices, each of which is stained with a single stain. A high resolution digital photograph is taken of each slice, and data from the resulting multiple digital images are then merged and "co-registered" in order to obtain a single digital image that is then usable as the digital image 9. For additional information on co-registration, see: 1) U.S. Patent Application Publication 2013/0156279, by Ralf Schoenmeyer et al., entitled "Evaluation of Co-Registered Images of Differently Stained Tissue Slices", published on Jun. 20, 2013; and U.S. Pat. No. 8,699,769, by Ralf Schoenmeyer et al., entitled "Generating Artificial Hyperspectral Images Using Correlated Analysis Of Co-Registered Images", issued on Apr. 15, 2014 (the entire subject matter of each of these patent documents is hereby incorporated by reference). In another example, a tissue slice stained with the immunofluorescence technique using multiple antibodies with respective, spectrally different dyes (fluorophores) is used to generate the digital image 9. By using immunofluorescence with multiple antibodies and dyes, ambiguities in the detection of the cell type can be resolved. When staining with anti-PDL1 and anti-CD68, the co-occurrence of both signals within a single cell indicates a PDL1 positive macrophage cell. When staining with anti-PDL1 and anti-CK18, the co-occurrence of both signals within a single cell indicates a PDL1 positive epithelial cell. This staining method therefore allows the researcher to investigate multiple elements of a pathway using a single slice. Similar to the brightfield immunohistochemistry example discussed above, multiple immunofluorecent stained slices may be co-registered to obtain the digital image 9. This method increases the number of elements of a pathway that can be observed to as many as one hundred (ten slices with ten antibodies each). Accordingly, various modifications, adaptations, and combinations of various features of the described embodiments can be practiced without departing from the scope of the invention as set forth in the claims.

What is claimed is:

1. A method involving a correlation value determining and visualization system, the method comprising:

(a) segmenting a digital image of a tissue slice of a cancer patient into first image objects representing immune cells and second image objects representing cancer cells, wherein the tissue slice was stained with a first antibody that is specific to a first protein present in immune cells, and wherein the tissue slice was stained with a second antibody that is specific to a second protein present in cancer cells;

(b) identifying a reference correlation value from among a plurality of reference correlation values indicative of protein-protein interactions in biochemical pathways, wherein the reference correlation value is indicative of a correlation between immune cells and cancer cells;

(c) identifying an image region in the digital image, wherein the image region is divided into a set of tiles;

(d) generating, for each tile, a first value and a second value, wherein the first value is indicative of a density of the first image objects in the tile, and wherein the second value is indicative of a density of the second image objects in the tile;

(e) determining, for the image region, a measured correlation value that is indicative of a relationship between the first value and the second value;

(f) comparing the measured correlation value determined in (e) with the reference correlation value identified in (b) and thereby generating a correspondence value; and (g) displaying the image region on a display of the system along with an associated visual indication representing the correspondence value determined in (f), wherein (a) through (g) are performed by the system.

2. The method of claim 1, wherein the system stores a plurality of reference correlation values, wherein the identifying of (b) involves receiving user input into the system, wherein the system then uses the user input to identify one of the plurality of reference correlation values to be the reference correlation value identified in (b).

3. The method of claim 1, wherein the identifying of (b) further involves displaying a representation of a biochemical pathway on the display of the system.

4. The method of claim 1, wherein the identifying of (b) further involves displaying a representation of a biochemical pathway on the display of the system, wherein the representation includes a plurality of user-selectable icons.

5. The method of claim 1, wherein the identifying of (b) further involve displaying to the user on the display of the system an indication of each pathway of a plurality of pathways, and soliciting the user to select one of the pathways.

6. The method of claim 1, wherein the identifying of (b) involves receiving user input into the system, wherein the user input is the reference correlation value.

7. The method of claim 1, wherein the identifying of (c) involves receiving user input into the system, wherein the system then uses the user input to identify the image region in the digital image.

8. The method of claim 1, wherein the identifying of (c) involves dividing the digital image into a two-dimensional array of identically-shaped image regions, wherein the image region identified in (c) is one of these identically-shaped image regions.

9. The method of claim 1, wherein the generating of (d), for each tile, involves counting the first image objects in the tile thereby generating a first count and counting the second image objects in the tile thereby generating a second count, wherein the first count is the first value, and wherein the second count is the second value.

10. The method of claim 1, wherein the determining of (e) is a determination of a Spearman's rank correlation coefficient.

11. The method of claim 1, wherein the correspondence value determined in (f) is indicative of the absolute value of a difference between the measured correlation value determined in (e) and the reference correlation value identified in (b).

12. The method of claim 1, wherein the visual indication of (g) is a shading of the image region, wherein a degree of the shading indicates the magnitude of the correspondence value.

13. The method of claim 12, wherein the visual indication of (g) further comprises a shading key, wherein the shading key indicates, for each possible shade of the image region, a corresponding correspondence value.

14. A method involving a correlation value determining and visualization system, the method comprising:
(a) receiving a digital image of a tissue sample of a cancer patient into the system, wherein the tissue sample includes first image objects stained with a first antibody stain, and wherein the tissue sample also includes second image objects stained with a second antibody stain;
(b) identifying in the digital image the first image objects;
(c) identifying in the digital image the second image objects;
(d) identifying a reference correlation value from among a plurality of reference correlation values indicative of protein-protein interactions in biochemical pathways, wherein the reference correlation value is indicative of a correlation between the first image objects and the second image objects;
(e) identifying an image region in the digital image, wherein the image region is divided into a set of tiles;
(f) generating, for each tile of the image region, a first value and a second value, wherein the first value is indicative of a density of the first image objects in the tile, and wherein the second value is indicative of a density of the second image objects in the tile;
(g) determining a measured correlation value indicative of a relationship between the first value and the second value;
(h) comparing the measured correlation value determined in (g) with the reference correlation value identified in (d) thereby generating a correspondence value; and
(i) displaying the image region on a display of the system along with an associated visual indication representing the correspondence value determined in (h), wherein (a) through (h) are performed by the system.

15. The method of claim 14, wherein the receiving of (a) is a storing of a digital image file into the system, and wherein the correspondence value generated in (h) is displayed in (i) as a visual indication of a difference between the measured correlation value determined in (g) and the reference correlation value identified in (d).

16. The method of claim 14, wherein the digital image represents a region, wherein the identifying of (e) is a dividing of the region of the digital image into a two-dimensional array of identically shaped image regions, wherein the image region identified in (e) is one of the image regions of the two-dimensional array.

17. The method of claim 14, wherein the identifying of the reference correlation value of (d) involves displaying a representation of a biochemical pathway on the display of the system, wherein the representation includes a plurality of user-selectable icons, and wherein the identifying of the correlation value of (d) further involves receiving user pathway icon selection information into the system.

18. A method involving a correlation value determining and visualization system, the method comprising:
(a) storing digital image information, of a tissue sample of a cancer patient on the system, wherein the tissue sample includes first image objects stained with a first stain, and wherein the tissue sample also includes second image objects stained with a second stain;
(b) storing a plurality of reference correlation values on the system that indicate how specified proteins correlate with other proteins in biochemical pathways, wherein one of the plurality of reference correlation values is indicative of a correlation between objects stained with the first stain and objects stained with the second stain;
(c) storing a plurality of measured correlation values on the system, wherein one of the measured correlation values is indicative of a correlation between the first image objects and the second image objects, wherein said one measured correlation value was generated by the system from the digital image information;
(d) receiving user input information into the system, wherein the user input information selects a biochemical pathway; and
(e) in response to the receiving in (d) causing a visual indication of a correspondence value to be displayed on a display of the system, wherein the correspondence value is indicative of a comparison of said one measured correlation value with said one of the plurality of reference correlation values, and wherein (a) through (e) are performed by the system.

19. The method of claim 18, further comprising:
(f) in response to the receiving of user input information in (d) causing a representation of the selected biochemical pathway to be displayed on the system, wherein the representation of the selected biochemical pathway includes a first pathway node icon and a second pathway node icon, wherein the first pathway node icon represents a first protein, wherein the second pathway node represents a second protein, and wherein the one reference correlation value in (e) is a reference correlation value of the first protein with respect to the second protein.

20. The method of claim 19, wherein the first pathway node icon is a user selectable icon, wherein the second pathway node icon is a selectable icon, wherein the user input information received in (d) includes information indicating that the first pathway node icon has been selected, and wherein the user input information received in (d) further includes information indicating that the second pathway node icon has been selected.

21. The method of claim 1, wherein the reference correlation value quantifies a strength of the relationship between the first image objects and the second image objects.

\* \* \* \* \*